US012662655B2

(12) United States Patent
Lundin et al.

(10) Patent No.:  US 12,662,655 B2
(45) Date of Patent:      Jun. 23, 2026

(54) DEVICE FOR DISTRIBUTING A FLOW

(71) Applicant: Cytiva Sweden AB, Uppsala (SE)

(72) Inventors: Andreas Lundin, Uppsala (SE); Bjorn Olovsson, Uppsala (SE); Klaus Gebauer, Uppsala (SE); Tim Francois, Uppsala (SE); Kerstin Erickson, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 1254 days.

(21) Appl. No.: 17/296,726

(22) PCT Filed: Dec. 10, 2019

(86) PCT No.: PCT/EP2019/084322
§ 371 (c)(1),
(2) Date: May 25, 2021

(87) PCT Pub. No.: WO2020/126639
PCT Pub. Date: Jun. 25, 2020

(65) Prior Publication Data
US 2022/0033750 A1     Feb. 3, 2022

(30) Foreign Application Priority Data

Dec. 19, 2018     (GB) ..................................... 1820691

(51) Int. Cl.
*C12M 1/00*          (2006.01)
*C12M 1/34*          (2006.01)
(52) U.S. Cl.
CPC ............ *C12M 23/40* (2013.01); *C12M 23/26* (2013.01); *C12M 23/28* (2013.01); *C12M 41/40* (2013.01)
(58) Field of Classification Search
CPC ...... C12M 23/40; C12M 23/26; C12M 23/28; C12M 41/40
See application file for complete search history.

(56) References Cited

U.S. PATENT DOCUMENTS 3,643,689  A      2/1972  Isreeli
4,879,029  A    11/1989  Whitehead
            (Continued)

FOREIGN PATENT DOCUMENTS

CN         1997553  A     7/2007
CN       101558259  A    10/2009
            (Continued)

OTHER PUBLICATIONS

Anthony K. Au, Hoyin Lai, Ben R. Utela and Albert Folch Microvalves and Micropumps for BioMEMS Micromachines 2011, 2, 179-220; doi:10.3390/mi2020179 (Year: 2011).*
            (Continued)

*Primary Examiner* — William H. Beisner
*Assistant Examiner* — Danielle B Henkel
(74) *Attorney, Agent, or Firm* — Eversheds-Sutherland (US) LLP

(57)                ABSTRACT

A flow distribution device for bioprocess systems, comprising: a flow distribution manifold (12; 112) comprising: at least four fluid connection conduits (14), wherein each fluid connection conduit (14) comprises a first end (18) for fluid connection and an opposite second end (20), and wherein at least three of the fluid connection conduits comprise a membrane (19*a*) and a valve seat (19*b*), which membrane (19*a*) can be put in at least two different positions in relation to the valve seat (19*b*) for allowing or preventing fluid flow between the first end (18) and the second end (20) of the fluid connection conduit (14); and a central common compartment (30) to which the second ends (20) of each of the fluid connection conduits (14) are connected, whereby the first ends (18) of each of the fluid connection conduits (14) can be in fluid communication with the central common compartment (30) and wherein the fluid connection conduits (14) are entering the central common compartment (30)
            (Continued)

from at least three different directions; wherein said flow distribution device (10) further comprises at least three membrane actuation members (41) which are provided in connection with one membrane (19*a*) of the flow distribution manifold (12; 112) each, wherein each of said membrane actuation members (41) is configured for actuating the membrane (19*a*) to be in at least two different positions in relation to the valve seat (19*b*), wherein a first position of the membrane (19*a*) allows flow between the first end (18) and the second end (20) of the fluid connection conduit (14) and a second position of the membrane (19*a*) prevents flow between the first end (18) and the second end (20) of the fluid connection conduit (14).

14 Claims, 10 Drawing Sheets

(56) References Cited

U.S. PATENT DOCUMENTS

| | | | |
|---|---|---|---|
| 6,554,806 | B2 | 4/2003 | Butterfield et al. |
| 7,846,335 | B2 | 12/2010 | Bisschops et al. |
| 9,869,400 | B2 * | 1/2018 | Schulz .................. F16K 11/105 |
| 2009/0218286 | A1 * | 9/2009 | Bisschops .............. G01N 30/20 |
| | | | 210/656 |
| 2014/0076454 | A1 | 3/2014 | Kjar |
| 2017/0029144 | A1 | 2/2017 | Kjar |
| 2017/0342364 | A1 * | 11/2017 | Grosch .................. C12M 23/40 |
| 2017/0361245 | A1 * | 12/2017 | Gebauer .............. G01N 30/467 |
| 2020/0061873 | A1 * | 2/2020 | Zumbrum ........... B29C 45/4407 |
| 2022/0025313 | A1 * | 1/2022 | Olovsson ............... C12M 29/00 |

FOREIGN PATENT DOCUMENTS

| | | |
|---|---|---|
| CN | 105814352 A | 7/2016 |
| CN | 106499841 A | 3/2017 |
| CN | 108757995 A | 11/2018 |
| DE | 102014226692 A1 | 6/2016 |
| EP | 1873520 A1 | 1/2008 |
| EP | 1948339 B1 | 6/2011 |
| JP | 63-078065 A | 4/1988 |
| JP | 2010-512490 A | 4/2010 |
| JP | 2010209962 A | 9/2010 |
| JP | 2015-518547 A | 7/2015 |
| JP | 2017-509834 A | 4/2017 |
| JP | 2018502302 A | 1/2018 |
| JP | 2022-514247 A | 2/2022 |
| WO | 1996012686 A2 | 5/1996 |
| WO | 1997012031 A1 | 4/1997 |
| WO | 98/45629 A1 | 10/1998 |
| WO | 2008073020 A1 | 6/2008 |
| WO | 2013/130176 A1 | 9/2013 |
| WO | 2013/147697 A1 | 10/2013 |
| WO | 2015095658 A1 | 6/2015 |
| WO | 2016043399 A1 | 3/2016 |
| WO | 2016096489 A1 | 6/2016 |

OTHER PUBLICATIONS

Japanese Office Action for JP Application No. 2021-534146 mailed Oct. 10, 2023 (20 pages).

Great Britain Search Report for GB Application No. 1820690.4 mailed Jun. 19, 2019 (6 pages).

Indian Office Action for IN Application No. 202117018220 mailed Jan. 5, 2023 (9 pages).

Indian Office Action for IN Application No. 202117018222 mailed Jan. 10, 2023 (6 pages).

International Search Report & Written Opinion for PCT Application No. PCT/EP2019/084321 mailed Apr. 28, 2020 (15 pages).

Chinese Office Action for CN Application No. 201980084557.9, dated Nov. 16, 2023 (12 pages).

Shi Xinhui, et al., "Simplified design of manifolds", Industrial Water & Wastewater, No. 4, pp. 60-65, Dec. 31, 1989 with English Translation.

Chinese Search Report for CN Application No. 201980084557.9, dated Nov. 9, 2023 (6 pages).

U.S. Office Action for corresponding U.S. Appl. No. 17/296,711, dated Aug. 29, 2024 (8 pages).

PCT International Search Report and Written Opinion for PCT/EP2019/084322 mailed Mar. 11, 2020 (11 pages).

Great Britain Search Report for GB Application No. 1820691.2 mailed Jun. 19, 2019 (6 pages).

Japanese Office Action and Search Report for JP Application No. 2021-534143 mailed Aug. 28, 2023 (11 pages).

* cited by examiner

DEVICE FOR DISTRIBUTING A FLOW

CROSS REFERENCE TO RELATED APPLICATIONS

This application claims the priority benefit of PCT/EP2019/084322, filed on Dec. 10, 2019, which claims the benefit of Great Britain Application No. 1820691.2, filed on Dec. 19, 2018, the entire contents of which are incorporated by reference herein.

TECHNICAL FIELD OF THE INVENTION

The present invention relates to a flow distribution device, a flow distribution manifold, a bioprocess separation system and a single use flow path for bioprocess systems.

BACKGROUND

Valve operated fluid delivery devices are for example used in liquid handling systems applied in the bioprocess field, for example in chromatography systems or filter systems. The valves can e.g. be diaphragm valves or pinch valves. For example at an inlet to a chromatography column there may be a need to connect a number of different fluid sources, such as for example different samples, washing fluids and elution fluid. Likewise, at an outlet of a chromatography column there may be a need to connect to a number of different fraction collectors. Diaphragm valves may be used in such liquid handling systems. A schematic illustration of a liquid handling system using diaphragm valves according to prior art is shown in FIG. 1. Four fluid modules 300 each comprising a T-shaped fluid conduit 302, two diaphragm valves 304 and two connectors 306 are shown connected to each other and to an external fluid conduit 308 and a pump P. With such a liquid handling system, four different fluid sources can for example be connected to an inlet of a chromatography system and, thanks to the provision of two diaphragm valves for each fluid source inlet, backflow and mixing can be avoided.

A problem with such a liquid handling system is that it is complex and comprises many valves. It may also be difficult to clean.

SUMMARY

An object of the present invention is to provide an improved flow distribution device.

A further object of the invention is to provide a flow distribution device with reduced risk for contamination and carry over.

This is achieved by a flow distribution device, a flow distribution manifold, a bioprocess separation system and a single use flow path according to the independent claims.

According to one aspect of the invention a flow distribution device for bioprocess systems is provided. Said flow distribution device comprises:

a flow distribution manifold comprising:

at least four fluid connection conduits, wherein each fluid connection conduit comprises a first end for fluid connection and an opposite second end, and wherein at least three of the fluid connection conduits comprise a membrane and a valve seat, which membrane can be put in at least two different positions in relation to the valve seat for allowing or preventing fluid flow between the first end and the second end of the fluid connection conduit; and a central common compartment to which the second ends of each of the fluid connection conduits are connected, whereby the first ends of each of the fluid connection conduits can be in fluid communication with the central common compartment and wherein the fluid connection conduits are entering the central common compartment from at least three different directions;

wherein said flow distribution device further comprises at least three membrane actuation members which are provided in connection with one membrane of the flow distribution manifold each, wherein each of said membrane actuation members is configured for actuating the membrane to be in at least two different positions in relation to the valve seat, wherein a first position of the membrane allows flow between the first end and the second end of the fluid connection conduit and a second position of the membrane prevents flow between the first end and the second end of the fluid connection conduit.

According to another aspect of the invention a flow distribution manifold is provided comprising:

at least four fluid connection conduits, wherein each fluid connection conduit comprises a first end for fluid connection and an opposite second end, and wherein at least three of the fluid connection conduits comprise a membrane and a valve seat, which membrane can be put in at least two different positions in relation to the valve seat for allowing or preventing fluid flow between the first end and the second end of the fluid connection conduit; and a central common compartment to which the second ends of each of the fluid connection conduits are connected, whereby the first ends of each of the fluid connection conduits can be in fluid communication with the central common compartment and wherein the fluid connection conduits are entering the central common compartment from at least three different directions, wherein said flow distribution manifold is configured for being used in a flow distribution device as described above.

According to another aspect of the invention a bioprocess separation system is provided comprising a separation device and at least one flow distribution device as described above connected to an inlet and/or an outlet of the separation device.

According to another aspect of the invention a single-use flow path is provided which is configured to be used in a bioprocess separation system as described above and comprising a flow distribution manifold as described above which is configured to be used in a flow distribution device as described above.

Hereby a flow distribution device is provided with a reduced number of diaphragm valves compared to prior art devices. Furthermore, cleaning of the flow distribution device is facilitated and the risk for contamination and carry over is hereby decreased thanks to the design comprising a central common compartment into which the fluid connections are entering from different directions, i.e. there is a common compartment provided in the middle of the device. Hereby a "distance" between different connections can be the same.

In one embodiment of the invention at least five fluid connection conduits are provided in the flow distribution manifold. In another embodiment of the invention at least six fluid connection conduits are provided in the flow distribution manifold.

In one embodiment of the invention the fluid connection conduits are entering the central common compartment from at least four different directions. In another embodiment of the invention the fluid connection conduits are entering the central common compartment from at least five different directions.

In one embodiment of the invention the second ends of the fluid connection conduits are connected to the central common compartment distributed around an enclosing wall of the central common compartment, which enclosing wall is enclosing an inner room of the central common compartment, wherein each of the fluid connection conduits can be in fluid communication with the inner room of the central common compartment and wherein the fluid connection conduits are entering the enclosing wall of the central common compartment from at least three different directions. In another embodiment the fluid connection conduits are entering the enclosing wall of the central common compartment from at least four different directions and in another embodiment the fluid connection conduits are entering the enclosing wall of the central common compartment from at least five different directions.

In one embodiment of the invention distances between the second ends of each of the fluid connection conduits and a central point of the central common compartment will not differ by more than 3 or 2 or 1 times an inner diameter (ID) of the fluid connection conduits. In one embodiment of the invention a distance between the second end of each of the fluid connection conduits and a central point of the central common compartment is substantially the same for each fluid connection conduit.

In one embodiment of the invention the flow distribution device comprises either the same number of membrane actuation members as the number of fluid connection conduits provided in the flow distribution manifold or one less, wherein one membrane actuation member is provided in connection with each fluid connection conduit or with each fluid connection conduit except one, whereby the flow through either all fluid connection conduits or all except one can be controlled by a membrane actuation member.

In one embodiment of the invention said flow distribution manifold is a single-use component.

In one embodiment of the invention said membrane actuation members are pressure controlling members.

In one embodiment of the invention said membrane actuation members are configured for being controlled by a connected control system, whereby the membrane actuation members can be controlled to actuate the membranes such that the first end of one of the fluid connection conduits can be fluidly connected with the first end of another one of the fluid connection conduits.

In one embodiment of the invention a flow distribution device is connected to an inlet of the separation device, wherein one fluid connection conduit of the flow distribution device is connected to the inlet of the separation device and at least three fluid connection conduits of the flow distribution device are connected to different fluid sources comprising fluids to be fed to the separation device.

In one embodiment of the invention a flow distribution device is connected to an outlet of the separation device, wherein one fluid connection conduit of the flow distribution device is connected to the outlet of the separation device and at least three fluid connection conduits of the flow distribution device are connected to different fraction collectors collecting different fractions from the separation device.

In one embodiment of the invention the bioprocess separation system comprises a reusable part comprising the membrane actuation members of the flow distribution device and at least one pump head and a single-use part comprising a single use flow path comprising the flow distribution manifold of the flow distribution device and optionally the separation device.

In one embodiment of the invention said single use flow path is pre-sterilized.

DETAILED DESCRIPTION OF EMBODIMENTS

Figure 1:
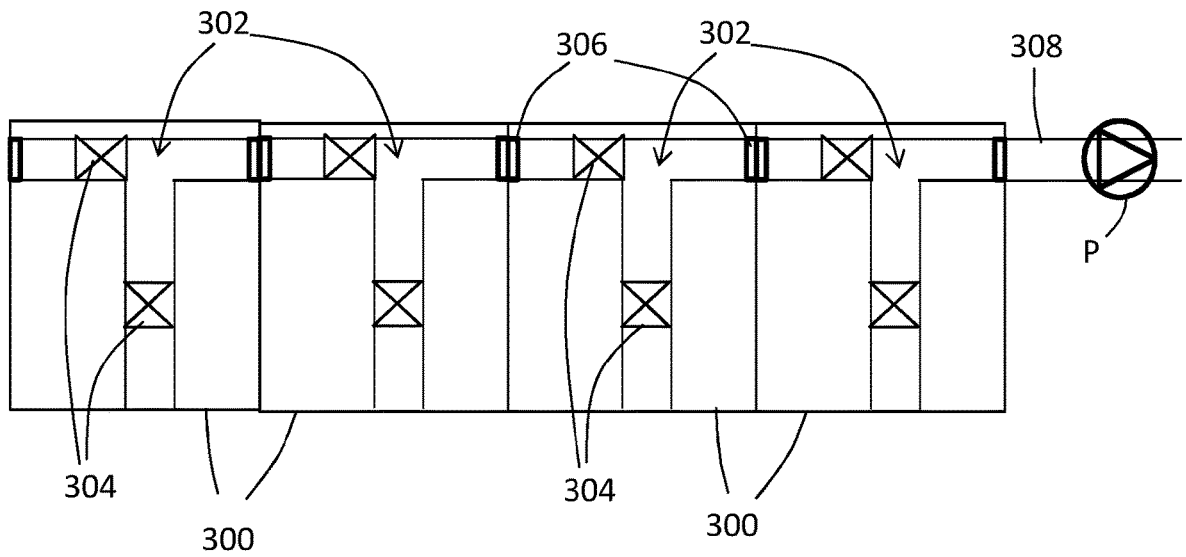
FIG. 1 shows schematically a device for delivery of fluid according to prior art.
Figure 2A:
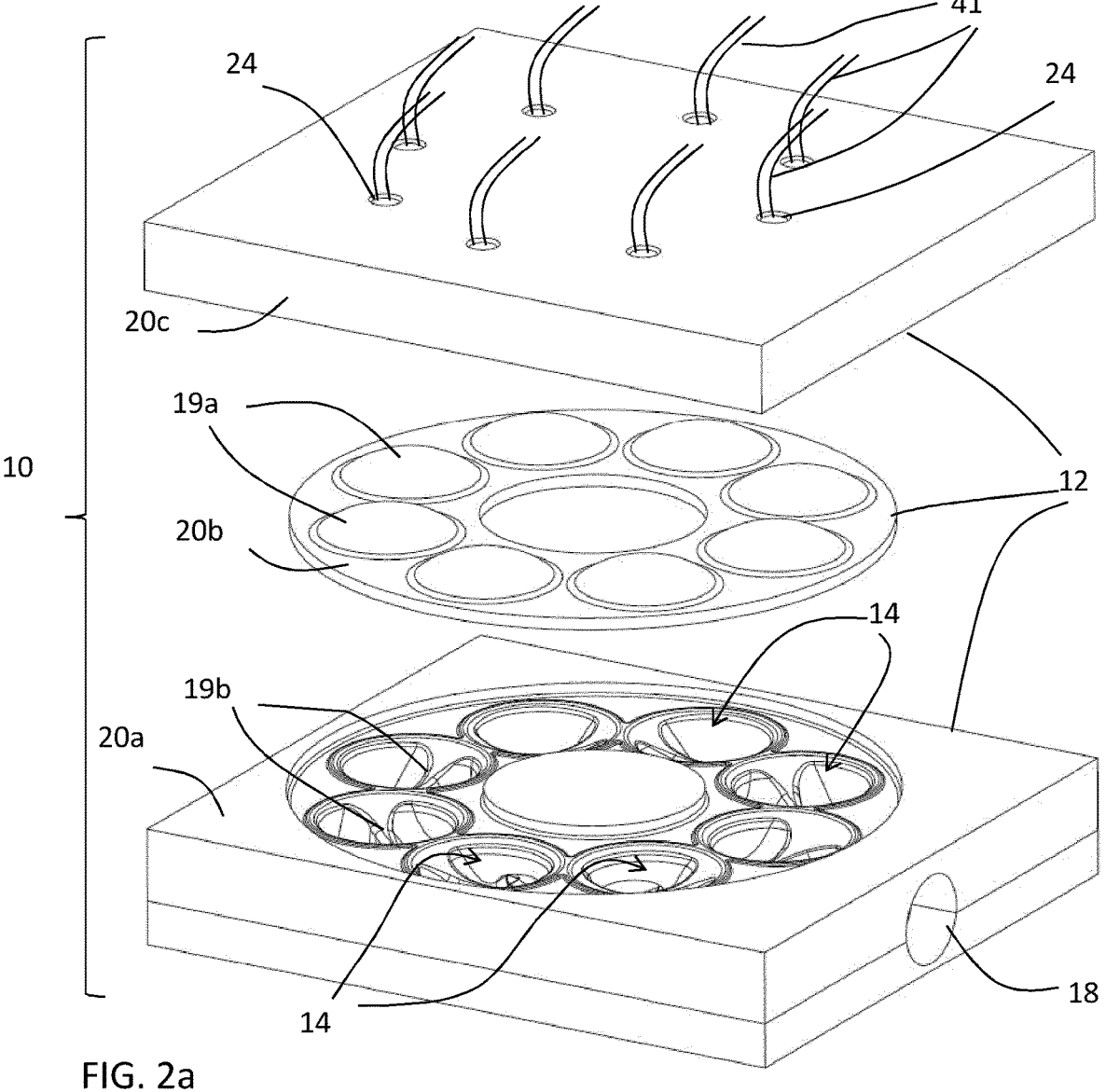
FIG. 2a is an exploded perspective view of a flow distribution device comprising a flow distribution manifold according to one embodiment of the invention.
Figure 2B:
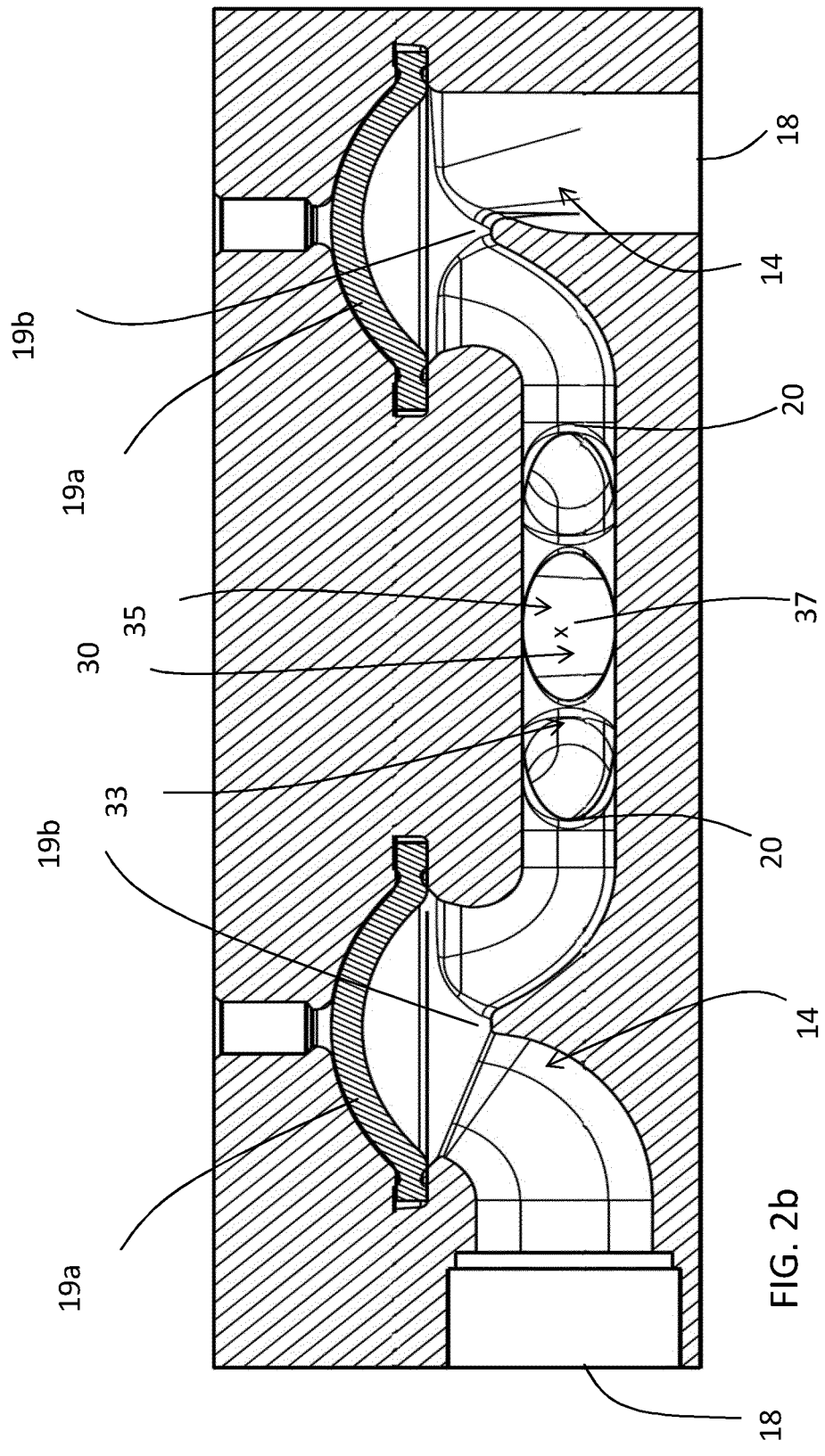
FIG. 2b is a cross section side view of the flow distribution manifold as shown in FIG. 2a as mounted.
Figure 2C:
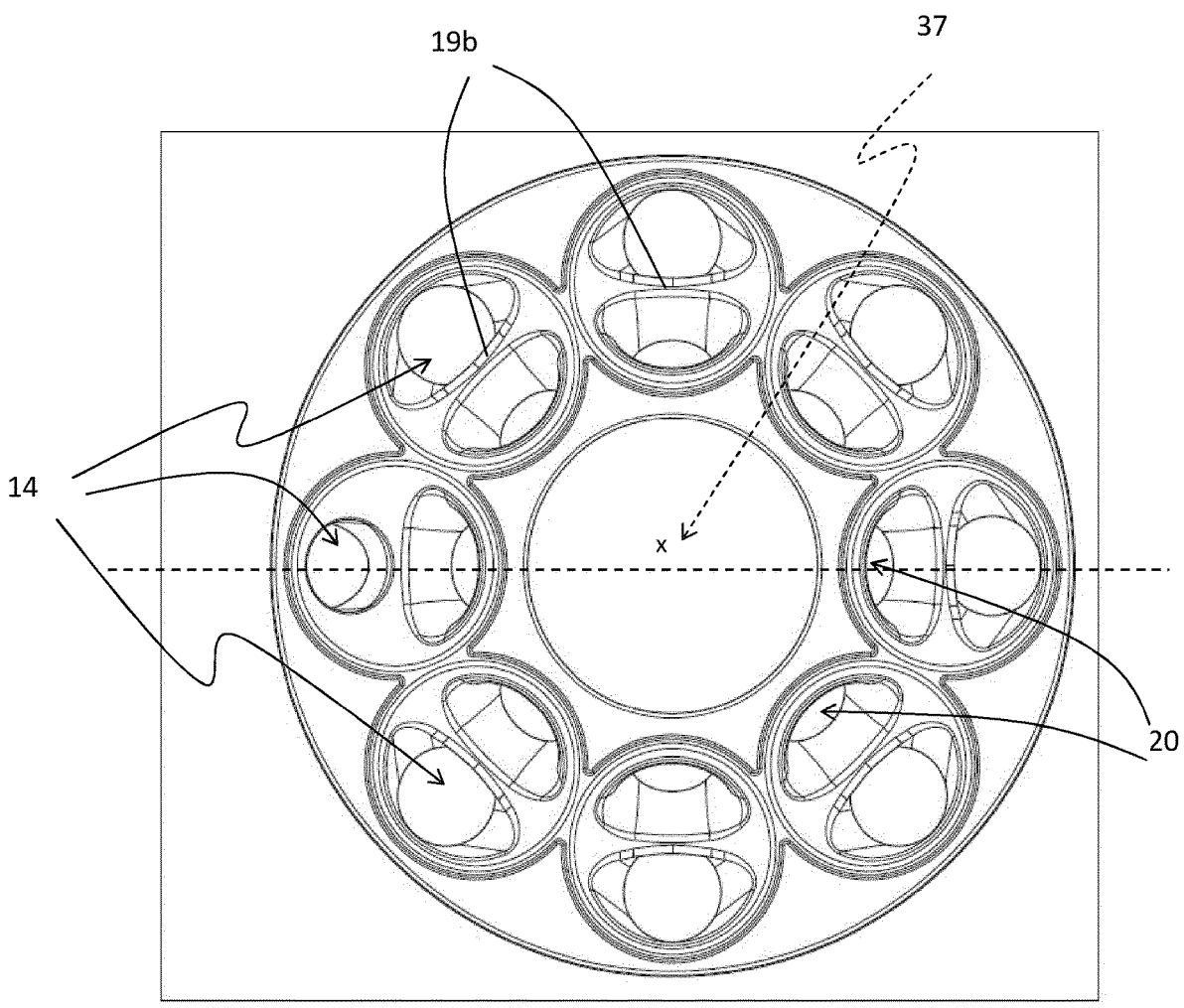
FIG. 2c is a top view of the flow distribution manifold as shown in FIGS. 2a and 2b without a cover and without membranes.
Figure 2D:
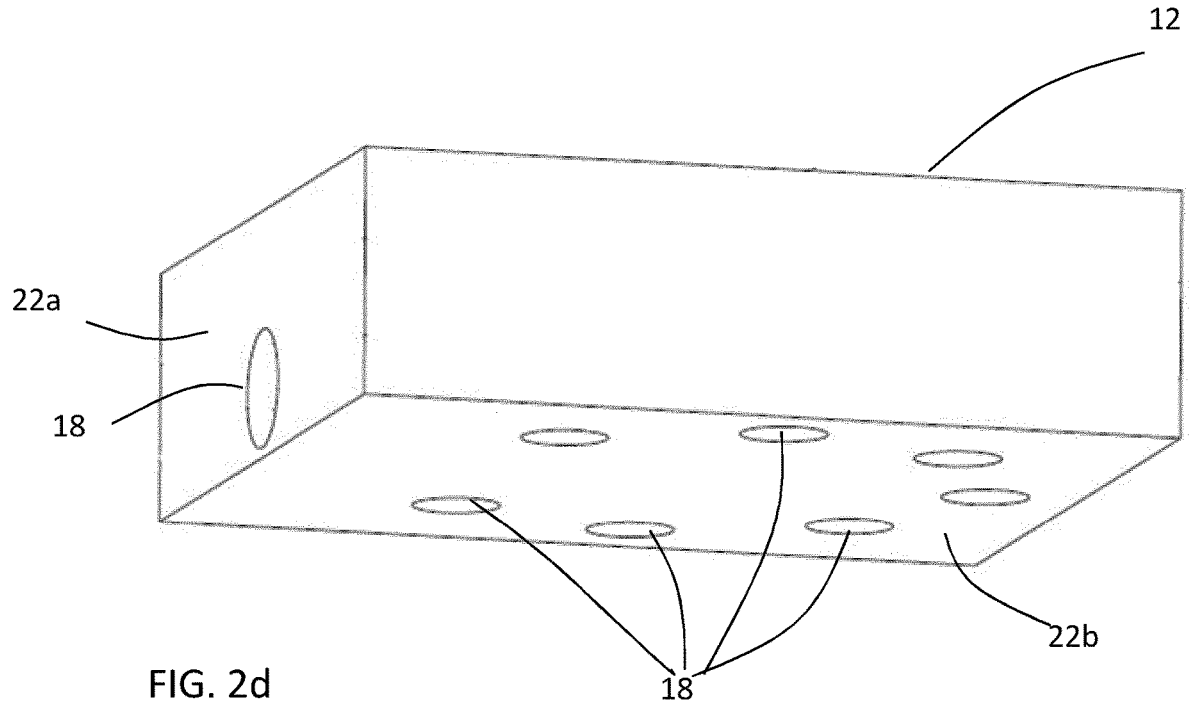
FIG. 2d is a perspective view of the flow distribution manifold as shown in FIGS. 2a-2c as mounted.
Figure 3A:
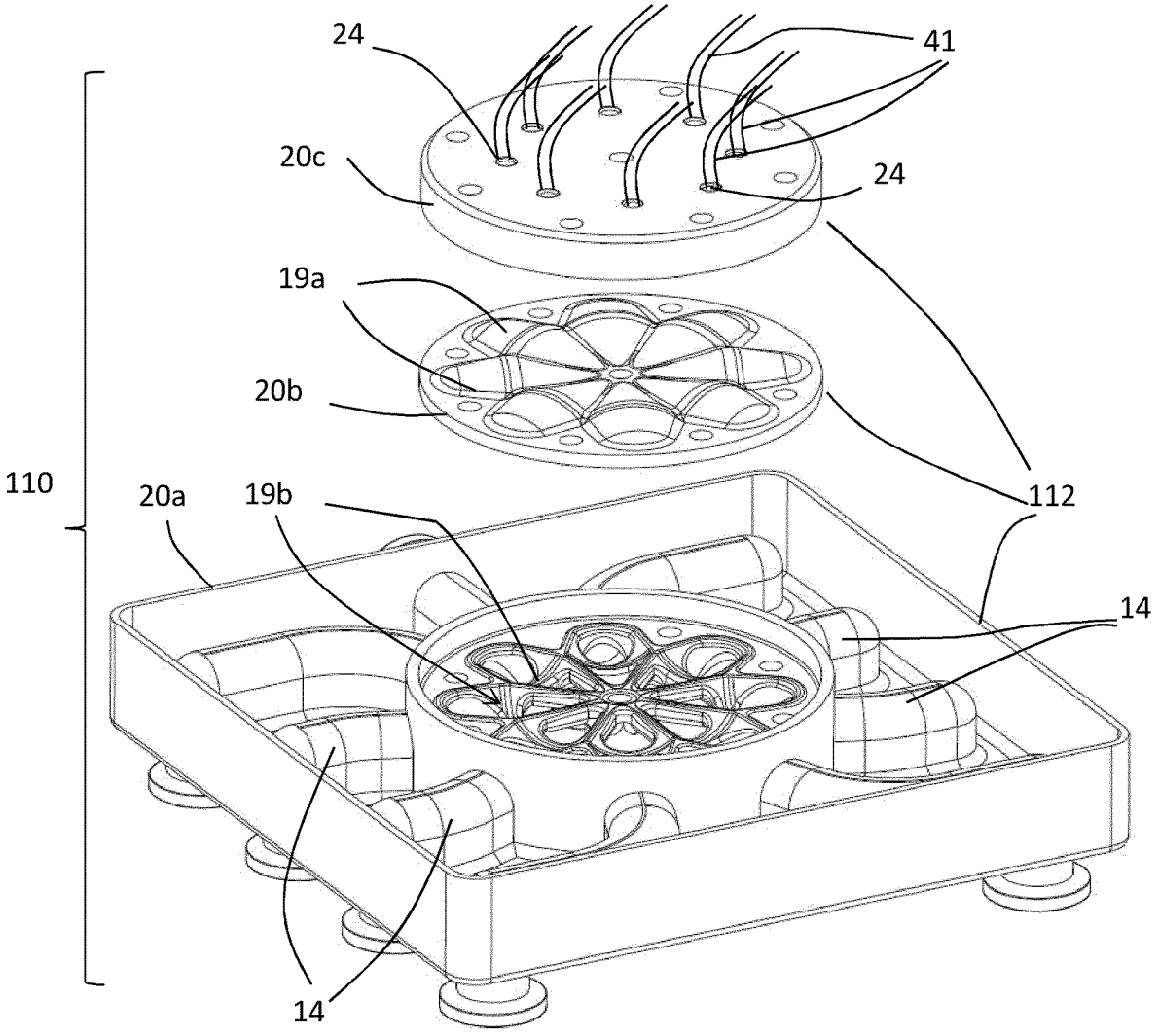
FIG. 3a is an exploded perspective view of a flow distribution device comprising a flow distribution manifold according to another embodiment of the invention.
Figure 3B:
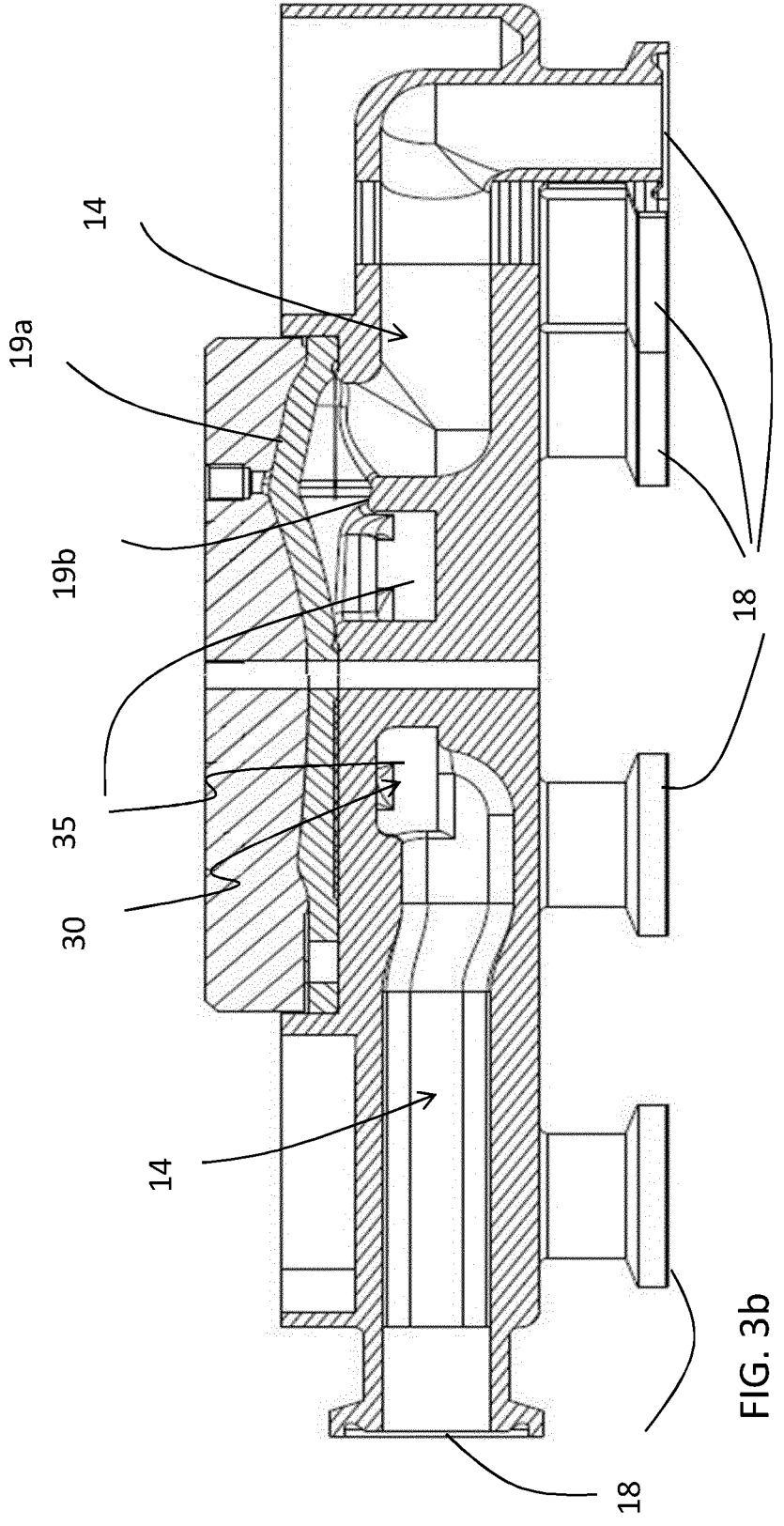
FIG. 3b is a cross section along the dotted lines in FIG. 3c of the flow distribution manifold as shown in FIG. 3a as mounted.
Figure 3C:
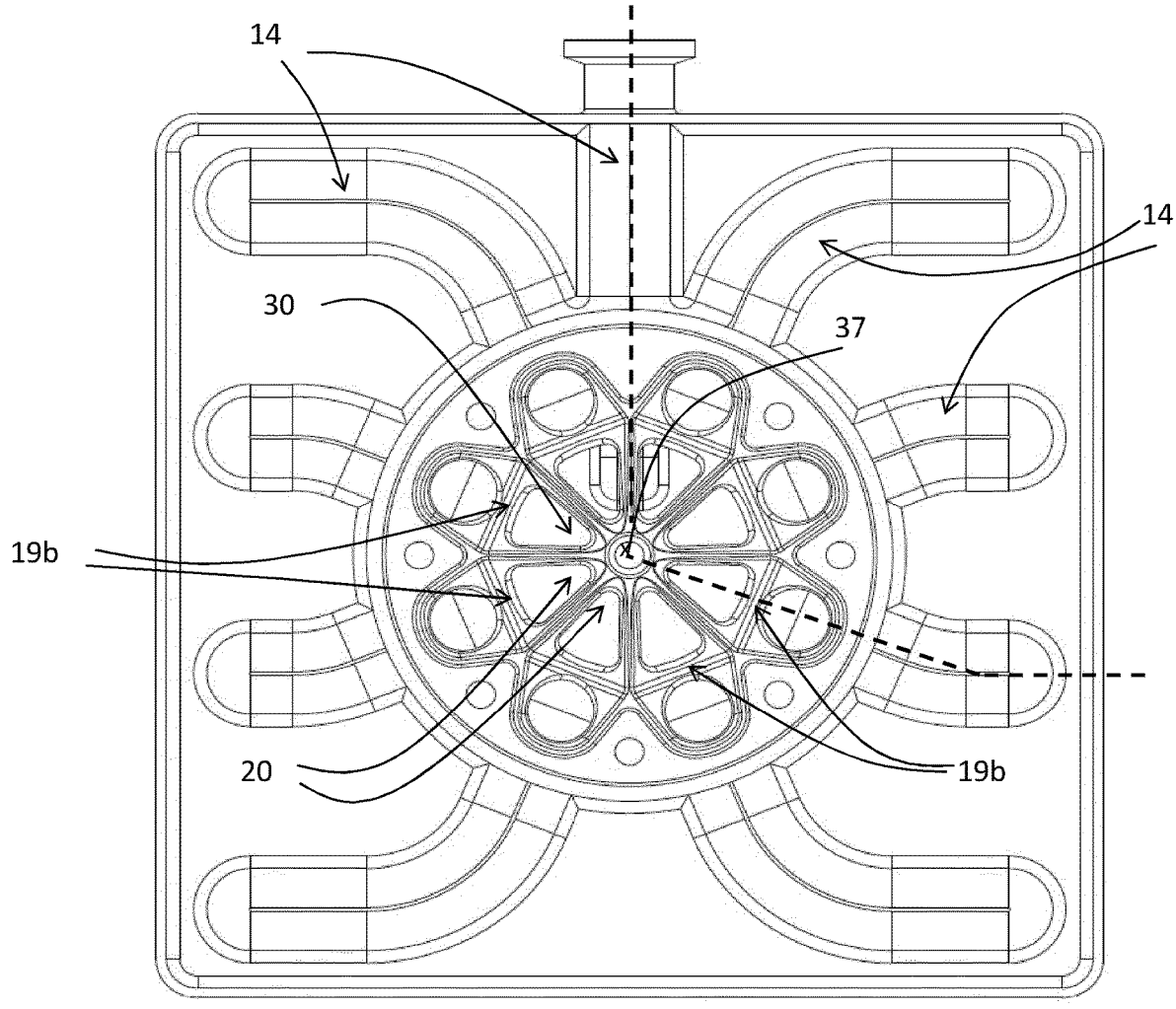
FIG. 3c is a top view of the flow distribution manifold as shown in FIGS. 3a and 3b without a cover and without membranes.
Figure 3D:
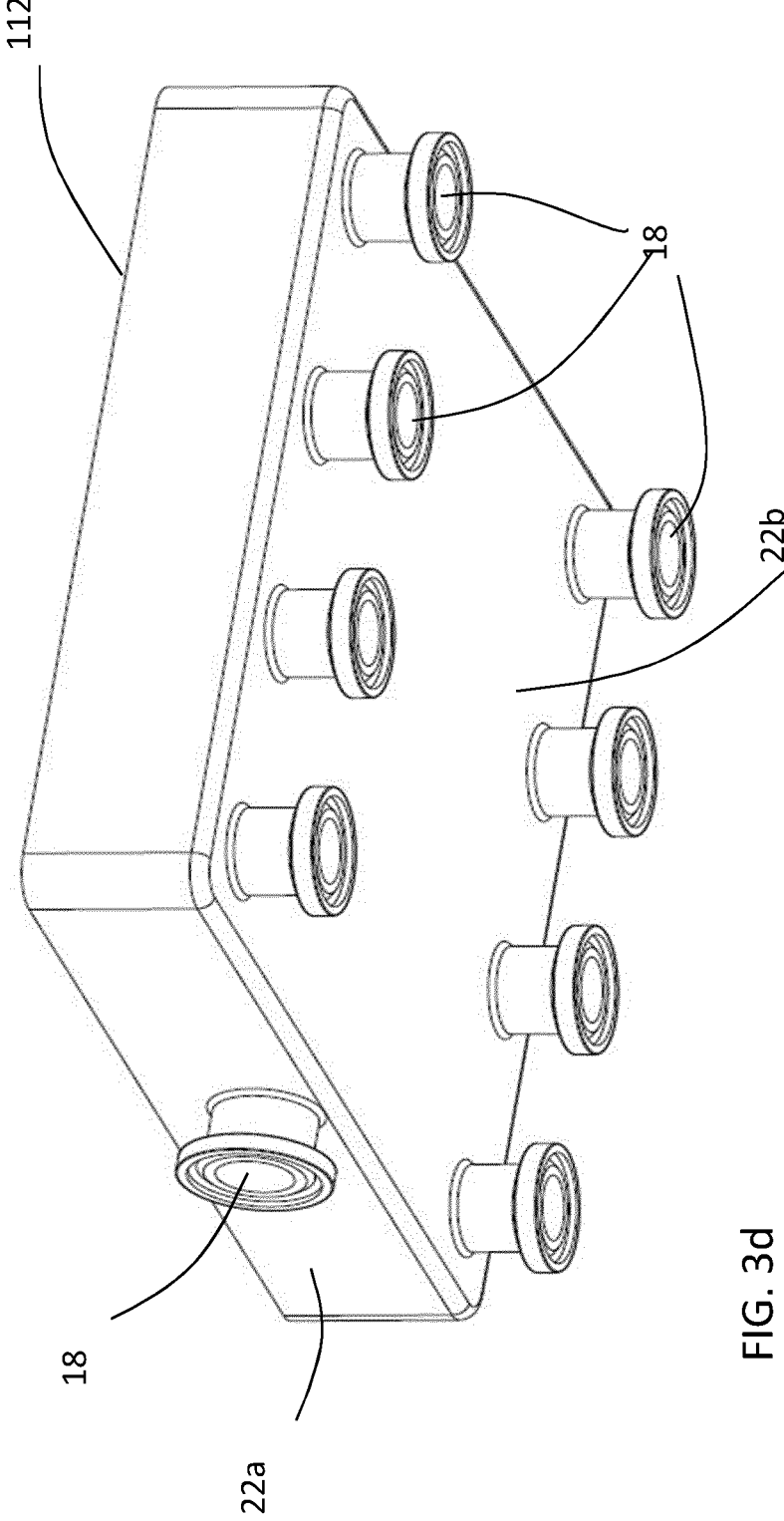
FIG. 3d is a perspective view of the flow distribution manifold as shown in FIGS. 3a-3c as mounted.

FIGS. 2a-2d show views of a fluid distribution device 10 and a fluid distribution manifold 12 according to one embodiment of the invention. FIGS. 3a-3d show different views of a fluid distribution device 110 and a fluid distribution manifold 112 according to another embodiment of the invention. FIGS. 2a and 3a show exploded perspective views of the fluid distribution device 10; 110, FIGS. 2b and 3b are cross section side views of the fluid distribution manifolds 12; 112 along the dotted lines of FIGS. 2c and 3c respectively. FIGS. 2c and 3c are top views of the fluid distribution manifolds 12; 112 without membranes provided and FIGS. 2d and 3d are perspective view of the fluid distribution manifolds 12; 112 as mounted. The two different embodiments will be described together below and the same reference numbers will be used for corresponding parts in the two different embodiments.

The fluid distribution device 10; 110 comprises one part which can be a single-use part. This is called a fluid distribution manifold 12; 112 and comprises at least four fluid connection conduits 14. In another embodiment the fluid distribution manifold comprises at least five or at least six fluid connection conduits 14. Each fluid connection conduit 14 comprises a first end 18 for fluid connection and an opposite second end 20. In the embodiment as shown in FIGS. 2a-2d eight fluid connection conduits 14 are shown and in the embodiment as shown in FIGS. 3a-3d nine fluid connection conduits 14 are shown, however the number of fluid connection conduits can of course be different. In FIG. 2*b* two of the eight fluid connection conduits 14 of this embodiment are shown in cross section. The first ends 18 and the second ends 20 of these two fluid connection conduits 14 can also be seen in FIG. 2*b*. In FIG. 3*a*, nine fluid connection conduits 14 can be seen. In FIGS. 2*d* and 3*d*, all the first ends 18 of the fluid connection conduits 14 can be seen. In one embodiment of the invention at least all fluid connection conduits 14 except one comprise a membrane 19*a* and a valve seat 19*b*, which membrane 19*a* can be put in at least two different positions in relation to the valve seat 19*b* for allowing or preventing fluid flow between the first end 18 and the second end 20 of this fluid connection conduit 14. In alternative language, membrane 19*a* is movable between an open position (at a distance from valve seat 19*b*) and a closed position (in sealing abutment with valve seat 19*b*). In the open position, fluid flow between first end 18 and second end 20 is allowed and in the closed position it is prevented. Of course also all fluid connection conduits 14 can comprise a membrane 19*a* and a valve seat 19*b* or optionally also all fluid conduits except two comprise a membrane 19*a* and a valve seat 19*b*. It can also be expressed, as in the claims, that at least three of the fluid connection conduits 14 when there are at least four fluid connection conduits 14 comprise a membrane 19*a* and a valve seat 19*b*. Actuation of the membranes 19*a* into the at least two different positions is provided from membrane actuation members 41 provided in the fluid distribution device 10; 110 as will be further described below.

Figure 5:
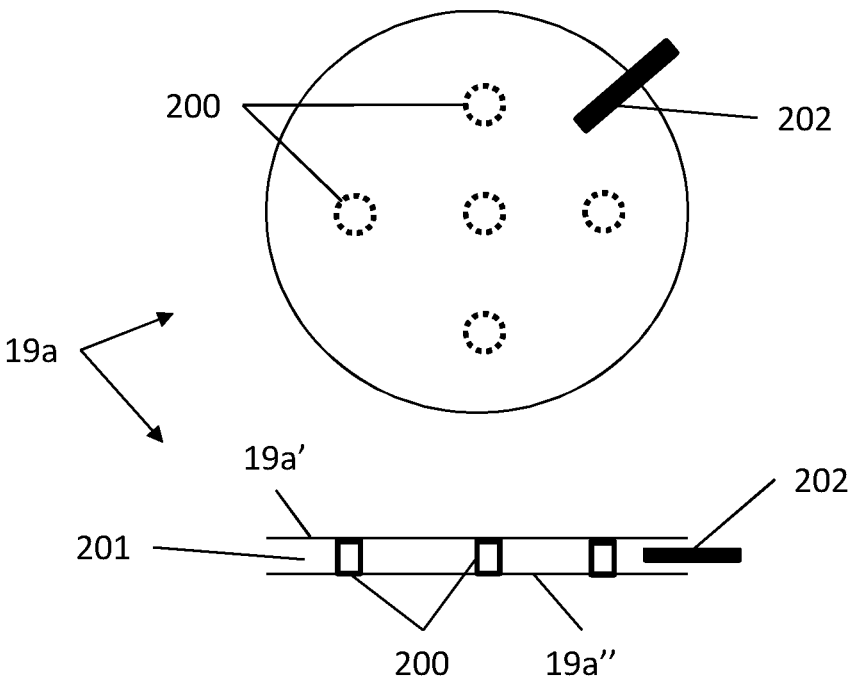
FIG. 5 shows a double-layer membrane according to an embodiment of the invention.

In certain embodiments, the membranes 19*a*, such as each membrane 19*a*, may comprise double-layered membranes. As shown in FIG. 5, a membrane 19*a* can then comprise the two membrane components 19*a*' and 19*a*". This mitigates the risk for inappropriate fluid flows in case one membrane component ruptures. Further, the components 19*a*' and 19*a*" may be spaced apart by a pattern of spacer elements 200, which can e.g. be studs, pillars, ribs etc. In the space 201 between the components a fluid sensor 202 (e.g. a conductivity sensor, pressure sensor etc.) can then be inserted to detect the presence of fluid due to the rupture of one of the components 19*a*' and 19*a*".

According to the invention the fluid distribution manifold 12; 112 further comprises a central common compartment 30 to which the second ends 20 of each of the fluid connection conduits 14 are connected, whereby the first ends 18 of each of the fluid connection conduits 14 can be in fluid communication with the central common compartment 30, i.e. when the corresponding membranes 19*a* are in the first (open) position. Furthermore, according to the invention the fluid connection conduits 14 are entering the central common compartment 30 from at least three different directions. In another embodiment of the invention the fluid connection conduits 14 are entering the central common compartment 30 from at least four or at least five different directions. In the embodiments shown in FIGS. 2*a*-2*d* and in FIGS. 3*a*-3*d* all the fluid connection conduits 14 are entering the central common compartment 30 from different directions and the fluid distribution manifold 12 has a star-like configuration with the fluid connection conduits 14 pointing away from the central common compartment 30 in different directions. In the embodiments shown in FIGS. 2 and 3 the fluid connection conduits 14 are all provided in one and the same plane when entering into the central common compartment 30 but they could as well be provided in different planes, i.e. the second ends 20 of the fluid connection conduits 14 can be connected to the central common compartment 30 distributed around an enclosing wall 33 of the central common compartment 30, which enclosing wall 33 is enclosing an inner room 35 of the central common compartment 30, wherein each of the fluid connection conduits 14 can be in fluid communication with the inner room 35 of the central common compartment 30, when the corresponding membranes 19*a* are in the first (open) position), and wherein the fluid connection conduits 14 are entering the enclosing wall 33 of the central common compartment 30 from at least two or three or four different directions. In the embodiments of the invention shown in FIGS. 2 and 3 the fluid connection conduits 14 are entering the enclosing wall 33 of the central common compartment 30 from eight and nine different directions respectively. As discussed above, fluid connection conduits could as well be provided entering the central common compartment 30 from all directions, i.e. for example entering the central common compartment in a direction being substantially perpendicular in relation to the fluid connection conduits as shown in FIGS. 2 and 3. The central common compartment 30 can have a form of a sphere or a spheroid which is the case in the embodiment as shown in FIGS. 2*a*-2*d* or be annular as is the case in the embodiment shown in FIGS. 3*a*-3*d*.

The flow distribution device 10; 110 further comprises at least three membrane actuation members 41 which are provided in connection with one membrane 19*a* of the flow distribution manifold 12; 112 each. In the embodiment of the invention as shown in FIGS. 2*a*-2*d* one membrane actuation member 41 is provided for each fluid connection conduit 14, i.e. eight membrane actuation members 41 are provided in the flow distribution device 12. In the embodiment of the invention as shown in FIGS. 3*a*-3*d* all fluid connection conduits 14 except one are provided with a membrane actuation member 41.

Each of said membrane actuation members 41 is configured for actuating the membrane 19*a* to be in at least two different positions in relation to the valve seat 19*b*, wherein a first position of the membrane 19*a* allows flow between the first end 18 and the second end 20 of the fluid connection conduit 14 and a second position of the membrane 19*a* prevents flow between the first end 18 and the second end 20 of the fluid connection conduit 14.

The membrane actuation members 41 can be for example pressure controlling members such as tubes through which pressurized air or suction can be provided. Hereby the membranes can be controlled into the at least two different positions by controlling pressure in the membrane actuation members 41. Another alternative of membrane actuation members 41 can be some kind of rods in mechanical connection with the membranes whereby a displacement of the rod can be transferred to displacement of the membranes.

The membrane actuation members 41 can be configured for being controlled by a connected control system, whereby the positions of the membranes 19*a* in the fluid distribution manifold 12; 112 can be controlled form the control system such that the first end 18 of one of the fluid connection conduits 14 can be fluidly connected with the first end 18 of another one of the fluid connection conduits 14. In one embodiment of the invention the first end 18 of any one of the different fluid connection conduits 14 can be connected with the first end 18 of any one of the other fluid connection conduits 14.

The membranes 19*a* and valve seats 19*b* are suitably provided at a position of the fluid connection conduits 14 close to the second ends 20 of the fluid connection conduits 14. The distance d1 between the valve seat 19*b* and the second end 20 of the fluid connection conduit 14 can for example be less than four or less than three or less than two fluid connection tube 14 inner diameters ID.

In some embodiments of the invention the distances between the second ends 20 of each of the fluid connection conduits 14 and a central point 37 of the central common compartment 30 will not differ by more than 3 or 2 or 1 times an inner diameter, ID, of the fluid connection conduits 14. In the embodiments as shown in FIGS. 2a-2d and in FIGS. 3a-3d the central common compartment 30 is symmetrical and the fluid connection conduits 14 are positioned symmetrical around the central common compartment 30 at substantially the same distance from a central point 37 of the central common compartment 30, i.e. a distance between the second end 20 of each of the fluid connection conduits 14 and a central point 37 of the central common compartment 20 is substantially the same for each fluid connection conduit 14.

A difference from prior art flow delivery manifolds is that in prior art the fluid connections were provided in parallel while in this new invention at least some of the fluid connection conduits are provided in different directions, i.e. at least some of the fluid connection conduits 14 are spread out from the central common compartment 30. Hereby a distance from a center of the second end 20 of at least one of the fluid connection conduits 14 to a center of the second end 20 of an adjacent fluid connection conduit 14 is smaller than the distance between central points of two membranes 19a provided to the same two fluid connection conduits 14.

The flow distribution manifold 12; 112 can be a single-use component. It can be molded from a suitable material, such as for example a polymer, and it can be provided with aseptic connectors for aseptic connection in a system. The flow distribution manifold 12; 112 can be pre-sterilized for example by gamma radiation or other sterilization methods, optionally together with other parts of a single-use flow path to be used for example in a bioprocess separation system, such as a chromatography system or a filter system as will be further described below.

Another part of the flow distribution device 10; 110 can be a reusable part and this part comprises the membrane actuation members 41.

The flow distribution manifold 12; 112 can comprise three parts as disclosed in the exploded views is FIGS. 2a and 3a. A first part 20a comprises the fluid connection conduits 14, the valve seats 19b and the common compartment 30. In both the embodiment shown in FIGS. 2a-2d and the embodiment shown in FIGS. 3a-3d one of the fluid connection conduits 14 has its first end 18 entering towards a side edge 22a of the first part 20a and all the other fluid connection conduits 14 have their first ends 18 entering towards a bottom side 22b of the first part 20a, see FIGS. 2d and 3d. This may be suitable when connecting the fluid distribution device 10; 110 in a system, for example to an inlet or an outlet of a bioprocess separation system as will be further described in relation to FIG. 4 below. A second part 20b of the flow distribution manifold 12; 112 comprises the membranes 19a and a third part 20c of the flow distribution manifold 12; 112 comprises connections 24 for allowing connection to membrane actuation members 41 and mating them to one membrane 19a each.

Figure 4:
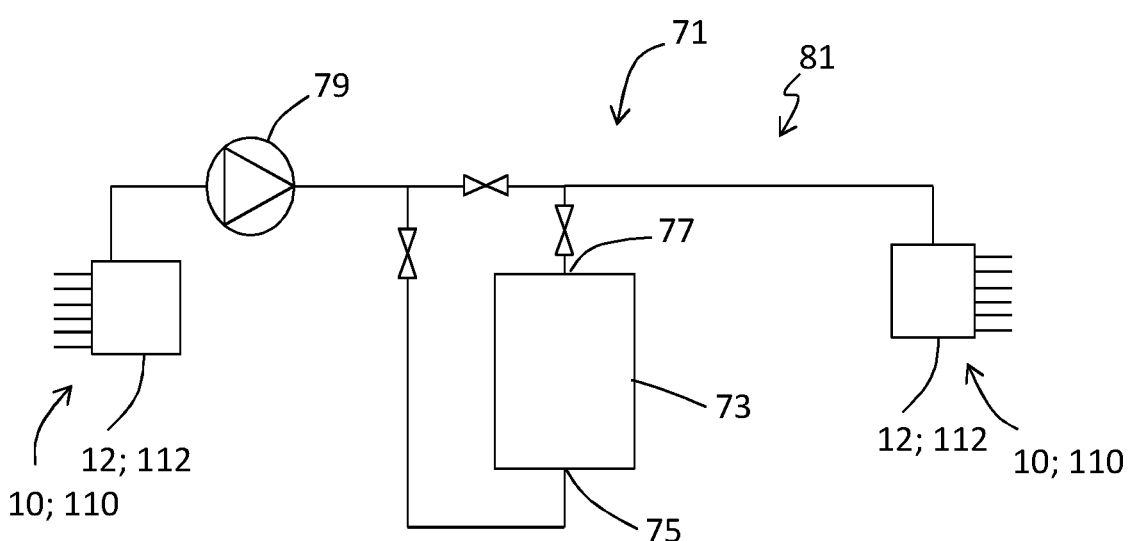
FIG. 4 shows schematically a bioprocess separation system in which a flow distribution device according to the invention can be used.

The present invention also relates to a bioprocess separation system 71 as schematically shown in FIG. 4, such as a chromatography system or a filter system, which comprises one or more fluid distribution devices 10; 110 as described above. One fluid distribution device 10; 110 can be connected to an inlet 75 of a separation device 73 provided in the bioprocess separation system 71 and/or one fluid distribution device 10; 110 can be connected to an outlet 77 of the separation device 73. The separation device 73 can for example be a chromatography column or a filter. At least one pump 79 is also provided in the bioprocess separation system 71. Other components such as valves and sensors are normally also provided in the bioprocess separation system 71 but will not be described in further detail here. A single-use flow path 81 comprising flow paths, the flow distribution manifold 12; 112 according to the invention and optionally also the separation device 73 is also part of the present invention, i.e. the flow distribution manifold 12; 112 can be connected to other flow paths of a bioprocess separation system and be pre-sterilized for easy connection and exchange in a bioprocess separation system 71. Reusable parts of the bioprocess separation system 71 are for example pump heads 79 and the membrane actuation members 41 of the flow distribution device 10; 110.

The central common compartment 30 of the fluid distribution manifold 12; 112 according to the invention can optionally be provided with a sensor, for example an air sensor, pressure sensor or a conductivity sensor.

The fluid distribution device 10; 110 according to the invention is compact and flexible. It can be positioned remote from a system where it is used because of the valve control provided by pressurized air.

As discussed above the flow distribution manifold is suitable for single-use applications. The flow distribution manifold, and optionally a single use flow path to which it can be connected, can be pre-sterilized by for example gamma radiation and can be provided with aseptic connectors for aseptic connection in a system.

The single-use technology (SUT) is important in the bioprocess industry in order to reduce production cost, increase production throughput and quality and to increase safety. With single-use processing technology and equipment, wetted parts that are in contact with the process fluid and drug product during processing, such as for example fluid storage vessels, tubing, separation equipment etc., are provided as clean and ready to use consumables which are to be installed and used for a specific process, product or over a limited time only and to be disposed thereafter.

SUT consumables are typically produced, configured and packaged in clean room environments to avoid contamination with microorganisms, particulates etc. SUT wetted parts can further be provided clean and pre-sterilized, thus allowing for aseptic and/or sterile processing, hereby reducing above mentioned risks relevant for product, operator or patient safety. Typically, SUT wetted parts are subjected to a sterilizing gamma irradiation treatment prior to use in the biomanufacturing process, and when doing so they are deployed as 'pre-sterilized' at the point of use. This may involve providing the consumable with a formal and validated sterile claim after the sterilizing treatment, however, it may alternatively involve providing a consumable that has undergone a sterilizing treatment but is provided without a formal sterile claim. With controlled and rigorous manufacturing conditions, SUT consumables may also be deployed non-sterile and/or with treatments that controls the state and condition of the consumable. Hereby, contamination levels by microorganisms, generally called 'bioburden', or levels of contamination or presence of contaminating substances or particles may be controlled and maintained within predefined levels.

The advantage of using single-use technology (SUT) fluid handling equipment is primarily that cross-contamination in between production batches and campaigns is eliminated when the SUT equipment is used for a single drug product only. The SUT equipment is disposed of after use, which can be after a single run, batch or campaign comprising multiple runs and batches. When providing SUT equipment pre-sterilized or by other means bioburden controlled, initial cleaning and sanitization (for example by contacting the flow path with sodium hydroxide solutions) or sterilization can be avoided. This enables a LEAN manufacturing approach, because time consuming, costly and non-value adding steps can be omitted. When using the SUT for a single run or batch only, even cleaning post-use may be omitted. The elimination of cleaning procedures and required cleaning fluids further reduces clean water requirements to prepare cleaning solutions in the first place, fluid handling and waste treatment, which translates to reduced facility size and complexity.

Single-use equipment may be provided with fluid connectors that enable closed processing and thereby protect the process fluid line and/or the operator and environment from contamination or exposure to hazardous substances. Alternatively, fluid connectors may be providing aseptic connectivity features, hereby providing strict and complete closure of the fluid lines. When using aseptic connectors or disconnectors, sterility of a fluid line, two connected lines or components, or two disconnected lines or components can be maintained, provided that the fluid lines or components involved in the operation have been provided sterile. With these features, SUT equipment allows not only for more efficient processing, it may also allow for reducing requirements on classification and containment of facilities, thereby reducing cost and risk for contamination or infection of the process fluid and drug product, and/or contamination and infection of the process environment, facility or the operator.

SUT systems provide higher flexibility in (re-)configuring a manufacturing facility and adapting it to different processes and products by design, i.e. through the reduced need for fixed installations compared to traditional processing systems and installations, which for example required auxiliary systems for CIP (Cleaning in Place) and SIP (Sterilization in place). Nowadays, SUT equipment and SUT processing regimes are therefore available or are being made available for the majority of all types of equipment and/or unit operations, among them bioreactors for cell culture or fermentation, buffer bags for liquid storage, tubing and pumps for liquid transfer and filling operations, filters, chromatography columns and related systems for separations.

With these features, SUT equipment does provide improved efficiency, safety and convenience compared to traditional installations and systems. Traditional installations and systems for processing are typically made from stainless steel and/or plastic and are not produced under controlled (or clean room) conditions reducing bioburden. Traditional systems are typically cleaned in place (CIP), sometimes also sterilized in place (SIP), which not only requires auxiliary installations, equipment and fluids, but involves also substantial time for validation, execution, and quality control of CIP and SIP procedures. The size, cost and complexity of facilities relying on traditional equipment and installations is significantly larger compared to production facilities deploying SUT. SUT facilities and processes can be planned, built and started up in significantly shorter time compared to traditional manufacturing technology, and SUT reduces capital investments and financial risk associated with a typically highly dynamic portfolio of drug products as well as risk and uncertainty related to the testing and approval of drug candidates and their product demand.

The invention claimed is:

1. A flow distribution device for bioprocess systems, comprising:
   a flow distribution manifold comprising:
      at least four fluid connection conduits, wherein each fluid connection conduit comprises a first end for fluid connection and an opposite second end, and wherein at least three of the fluid connection conduits comprise a membrane and a valve seat, which membrane can be put in at least two different positions in relation to the valve seat for allowing or preventing fluid flow between the first end and the second end of the fluid connection conduit; and
      a central common compartment to which the second ends of each of the fluid connection conduits are connected, whereby the first ends of each of the fluid connection conduits can be in fluid communication with the central common compartment and wherein the fluid connection conduits are entering the central common compartment from at least three different directions;
   wherein said flow distribution device further comprises at least three membrane actuation members which are provided in connection with one membrane of the flow distribution manifold each, wherein each of said membrane actuation members is configured for actuating the membrane to be in at least two different positions in relation to the valve seat, wherein a first position of the membrane allows flow between the first end and the second end of the fluid connection conduit and a second position of the membrane prevents flow between the first end and the second end of the fluid connection conduit;
   wherein the flow distribution manifold comprises three parts, a first part comprising the fluid connection conduits, the respective valve seats and the central common compartment, a second part comprising the membranes and a third part comprising connections for connection to the respective membrane actuation members and mating to a respective membrane; and
   wherein a distance between the second end of each of the at least four fluid connection conduits and a central point of the central common compartment is substantially the same for each of the at least four fluid connection conduits.

2. The flow distribution device according to claim 1, wherein at least five or at least six fluid connection conduits are provided in the flow distribution manifold.

3. The flow distribution device according to claim 1, wherein the fluid connection conduits are entering the central common compartment from at least four or at least five different directions.

4. The flow distribution device according to claim 1, wherein the second ends of the fluid connection conduits are connected to the central common compartment distributed around an enclosing wall of the central common compartment, which enclosing wall is enclosing an inner room of the central common compartment, wherein each of the fluid connection conduits can be in fluid communication with the inner room of the central common compartment and wherein the fluid connection conduits are entering the enclosing wall of the central common compartment from at least three or at least four or at least five different directions.

5. The flow distribution device according to claim 1, wherein distances between the second ends of each of the fluid connection conduits and a central point of the central common compartment will not differ by more than 3 or 2 or 1 times an inner diameter of the fluid connection conduits.

6. The flow distribution device according to claim 1, wherein the flow distribution device comprises either the same number of membrane actuation members as the number of fluid connection conduits provided in the flow distribution manifold or one less, wherein one membrane actuation member is provided in connection with each fluid connection conduit or with each fluid connection conduit except one, whereby the flow through either all fluid connection conduits or all except one can be controlled by a membrane actuation member.

7. The flow distribution device according to claim 1, wherein said flow distribution manifold is a single-use component.

8. The flow distribution device according to claim 1, wherein said membrane actuation members are pressure controlling members.

9. The flow distribution device according to claim 1, wherein said membrane actuation members are configured for being controlled by a connected control system, whereby the membrane actuation members can be controlled to actuate the membranes such that the first end of one of the fluid connection conduits can be fluidly connected with the first end of another one of the fluid connection conduits.

10. The flow distribution device according to claim 1, wherein each membrane is a double-layered membrane.

11. A bioprocess separation system comprising a separation device and at least one flow distribution device according to claim 1 connected to an inlet and/or an outlet of the separation device.

12. The bioprocess separation system according to claim 11, wherein the flow distribution device is connected to an inlet of the separation device, wherein one fluid connection conduit of the flow distribution device is connected to the inlet of the separation device and at least three fluid connection conduits of the flow distribution device are connected to different fluid sources comprising fluids to be fed to the separation device.

13. The bioprocess separation system according to claim 11, wherein a flow distribution device is connected to an outlet of the separation device, wherein one fluid connection conduit of the flow distribution device is connected to the outlet of the separation device and at least three fluid connection conduits of the flow distribution device are connected to different fraction collectors collecting different fractions from the separation device.

14. The bioprocess separation system according to claim 11, wherein the bioprocess separation system comprises a) a reusable part comprising the membrane actuation members of the flow distribution device and at least one pump head and b) a single-use part comprising a single use flow path comprising the flow distribution manifold of the flow distribution device and optionally the separation device.

* * * * *